(12) United States Patent
Wan

(10) Patent No.: US 9,435,760 B2
(45) Date of Patent: Sep. 6, 2016

(54) DETECTOR FOR DETECTING SODIUM HYPOCHLORITE CONCENTRATION

(71) Applicant: Senno Technology Inc., Hsinchu (TW)

(72) Inventor: Tin-Si Wan, Hsinchu (TW)

(73) Assignee: SENNO TECHNOLOGY INC., Hsinchu (TW)

(*) Notice: Subject to any disclaimer, the term of this patent is extended or adjusted under 35 U.S.C. 154(b) by 178 days.

(21) Appl. No.: 14/319,307

(22) Filed: Jun. 30, 2014

(65) Prior Publication Data

US 2015/0377816 A1    Dec. 31, 2015

(51) Int. Cl.
  *G01N 27/07* (2006.01)
  *G01N 27/403* (2006.01)
  *G01N 27/28* (2006.01)

(52) U.S. Cl.
  CPC ............. *G01N 27/07* (2013.01); *G01N 27/283* (2013.01)

(58) Field of Classification Search
  CPC ...... G01N 27/06; G01N 27/07; G01N 27/08; G01N 27/283; G01N 27/403
  See application file for complete search history.

(56) References Cited

U.S. PATENT DOCUMENTS 7,283,245 B2    10/2007    Xiao et al.
2015/0226721 A1*    8/2015    Son .................... G01N 33/18
                                                            324/694

FOREIGN PATENT DOCUMENTS

JP    02227183 A1 *    9/1990    ............... C02F 1/46
JP    09225468 A *    9/1997    ............... C02F 1/46

OTHER PUBLICATIONS

JPO computer-generated English language translation of the Abstract for Shinohara et al. JP 02-227183 A, patent published Sep. 10, 1990.*
JPO computer-generated English language translation of Tsuruata et al. JP 09-225468 A, patent published Sep. 2, 1997.*
Table of Contents and Chapter 27 of the GE on-line Handbook of Industrial Water Treatment (2012)(twelve pages) authors and editors unknown.*
Full Englsih language translation of Shinohara et al. JP 02227183 A, patent published Sep. 10, 1990.*

* cited by examiner

*Primary Examiner* — Alexander Noguerola
(74) *Attorney, Agent, or Firm* — Muncy, Geissler, Olds & Lowe, P.C.

(57) ABSTRACT

A detector for detecting sodium hypochlorite concentration includes a first electrode, a second electrode and a processing unit. The first electrode and the second electrode are disposed opposite each other, and are soaked in a sodium hypochlorite solution under detection. An electrical path is formed among the first electrode, the sodium hypochlorite solution and the second electrode. The processing unit, electrically connected to the first electrode and the second electrode, measures a plurality of ions in the sodium hypochlorite solution transmitted in the electrical path to obtain a conductivity of the sodium hypochlorite solution and to accordingly calculate concentration of the sodium hypochlorite solution. Compared to a conventional measurement apparatus adopting an optical detector, the invention not only can be fabricated at low production costs, but also can instantly obtain the detected concentration without involving analysis of an externally connected computer.

10 Claims, 5 Drawing Sheets

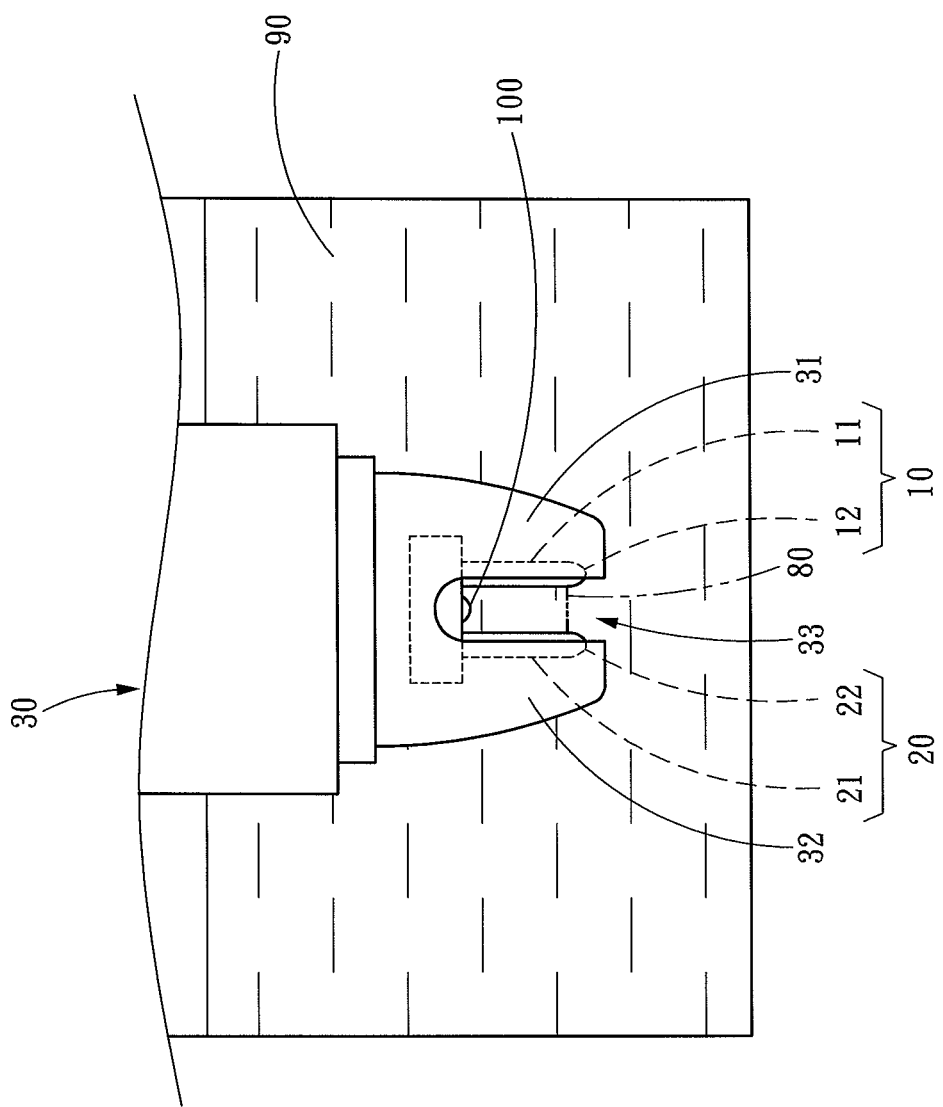

DETECTOR FOR DETECTING SODIUM HYPOCHLORITE CONCENTRATION

FIELD OF THE INVENTION

The present invention relates to a detector, and particularly to a detector for detecting sodium hypochlorite (NaOCl) concentration.

BACKGROUND OF THE INVENTION

Sodium hypochlorite (NaOCl) is effective for fighting against various viruses and bacteria, and solutions formed from sodium hypochlorite, e.g., bleach, are extensively adopted in various environments, utensils or foods with disinfection requirements. For example, solutions formed from sodium hypochlorite are applied to household cleaning, hospital disinfection, tableware or medical equipment disinfection, and food process bleaching. However, in bleach, the concentration of sodium hypochlorite needs to have different specified values in response to different application requirements. The concentration that is too low may fail to effectively provide adequate disinfection result, while the concentration that is too high may be hazardous to human bodies. Therefore, there is a need for measuring such concentration of the solution.

For example, in the U.S. Pat. No. 7,283,245, a system for measuring the concentration of multiple chemical or biological substances is disclosed. In the above disclosure, a disposable optical test element and a spectroscopic detector are adopted. The disposable optical test element is provided with a specific testing film having a constant spectrum reaction standard corresponding to a specific analyte. Through a change in light absorbance, luminescence, or other light-based forms of the specific analyte to the disposable optical test element, the spectroscopic detector detects the optical responses of the specific analyte to the disposable optical test element. Based on the spectrum reaction standard corresponding to the testing film, the concentration of the specific analyte can be measured. Thus, to measure the concentration of the sodium hypochlorite, the corresponding disposable optical test element is utilized.

The above optical measurement system is extremely costly. Further, the optical measurement system needs to be additionally connected to a computer in order to analyze the concentration of the analyte, in a way that a value of the concentration cannot be instantly obtained. As a result, the above optical measurement system may be inconvenient when being put to application.

SUMMARY OF THE INVENTION

As previously described, the above-mentioned conventional measurement apparatus is extremely costly, and needs to be additionally connected to a computer instead of being independently applied in order to obtain the value of the concentration. Therefore, the primary object of the present invention is to overcome the issues of such conventional measurement apparatus.

To achieve the above object, a detector for detecting sodium hypochlorite concentration is provided. The detector includes a first electrode, a second electrode, a housing and a processing unit. The first electrode and the second electrode are disposed opposite each other, and are soaked in a sodium hypochlorite solution under detection. An electrical path is formed among the first electrode, the sodium hypochlorite solution and the second electrode. The housing accommodates the first electrode and the second electrode. The first electrode includes a first detecting portion, which exposes outside the housing to extend outward. The second electrode includes a second detecting portion, which exposes outside the housing to extend outward. The housing includes a first outer wall disposed at one side of the first detecting portion away from the second detecting portion, a second outer wall disposed at one side of the second detecting portion away from the first detecting portion, and a measurement space formed between the first outer wall and the second outer wall and separating the first detecting portion from the second detecting portion. The first outer wall has a height greater than that of the first detecting portion. The second outer wall has a height greater than that of the second detecting portion. The electrical path is located in the measurement space. The processing unit, electrically connected to the first electrode and the second electrode, measures a plurality of ions in the sodium hypochlorite solution transmitted in the electrical path to obtain a conductivity of the sodium hypochlorite solution and to accordingly calculate concentration of the sodium hypochlorite solution.

As such, with the first electrode, the second electrode and the processing unit of the present invention, the ions in the sodium hypochlorite solution transmitted in the electrical path can be measured to obtain the conductivity and to further calculate the concentration of the sodium hypochlorite solution. Compared to a conventional measurement apparatus adopting an optical detector, the detector of the present invention not only can be fabricated at low production costs, but also can instantly obtain the detected concentration through standalone measurement instead of having to be additionally connected to and analyzed by a computer to provide better convenience. The present invention further offers an advantage of having a small volume for better portability. Further, with the first outer wall, the second outer wall and the measurement space of the present invention, the electrical path in the measurement space is measured, thereby preventing unnecessary disturbances outside the first outer wall and the second outer wall from affecting the measurement for the concentration.

The foregoing, as well as additional objects, features and advantages of the invention will be more readily apparent from the following detailed description, which proceeds with reference to the accompanying drawings.

BRIEF DESCRIPTION OF THE DRAWINGS

FIG. 5 is a schematic diagram of measuring concentration of a sodium hypochlorite solution according to an embodiment of the present invention

DETAILED DESCRIPTION OF THE PREFERRED EMBODIMENTS

Figure 1:
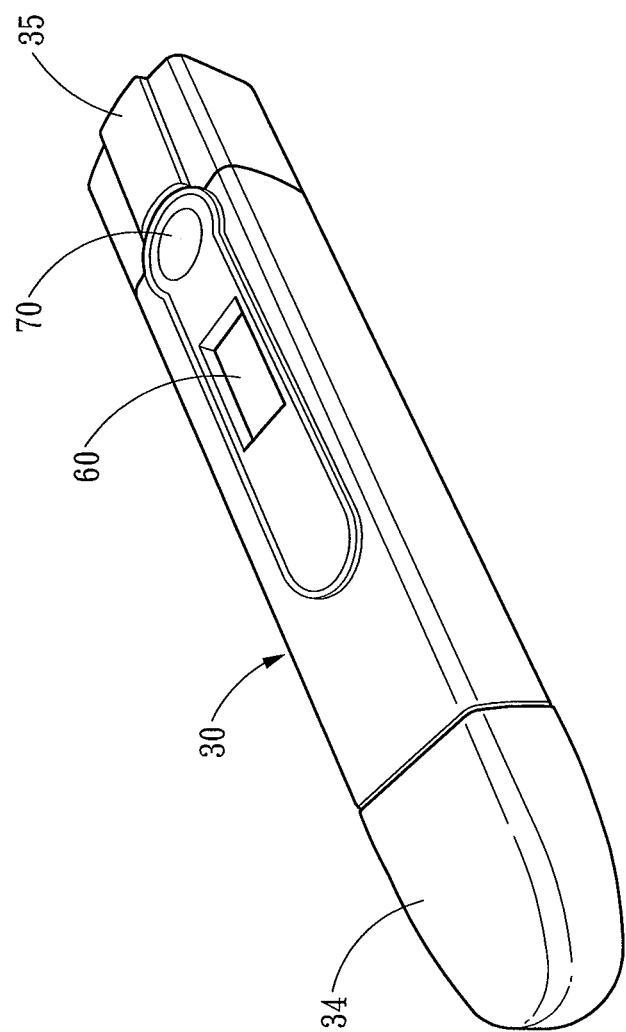
FIG. 1 is a schematic diagram of an appearance according to an embodiment of the present invention.
Figure 2:
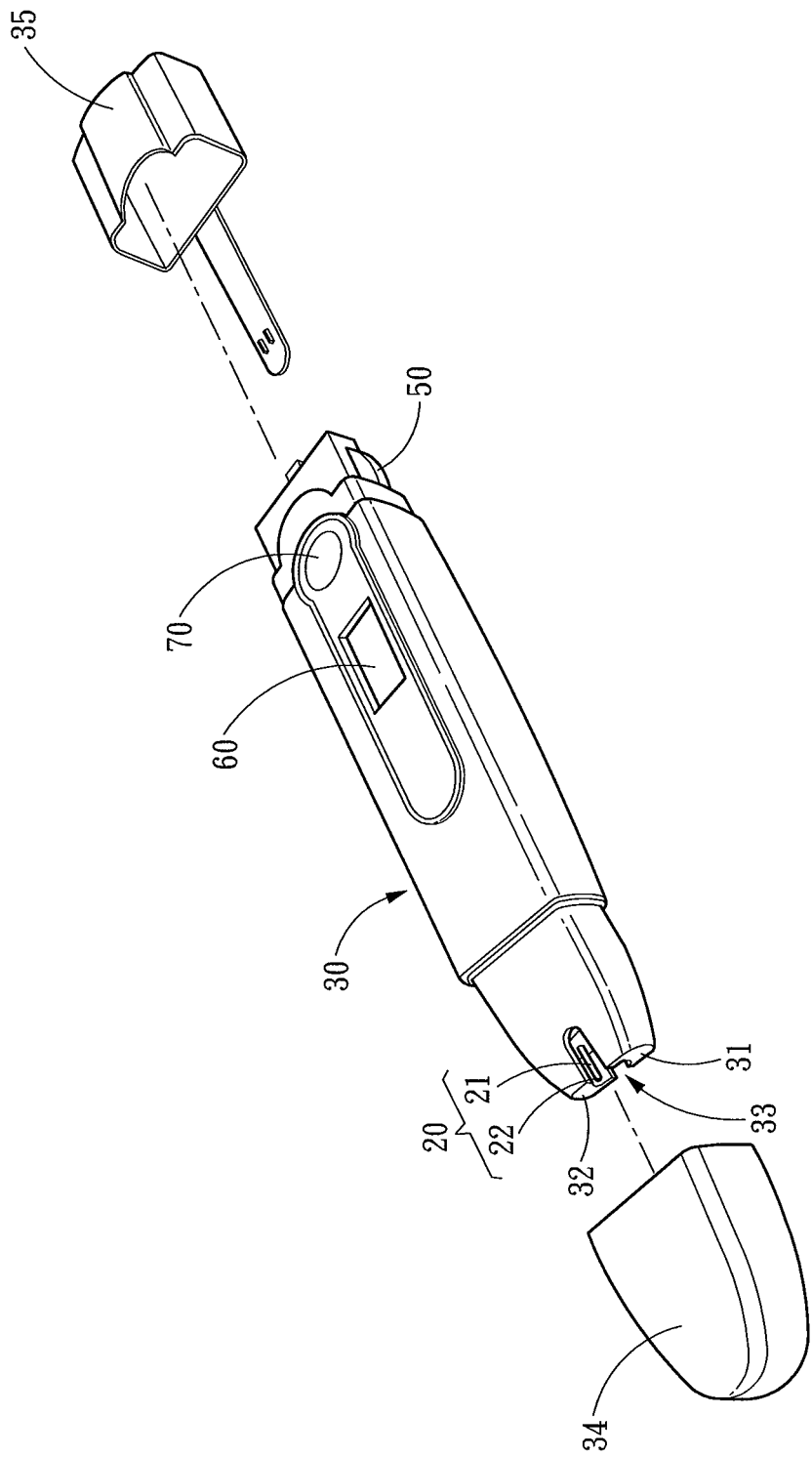
FIG. 2 is an exploded view according to an embodiment of the present invention.
Figure 3:
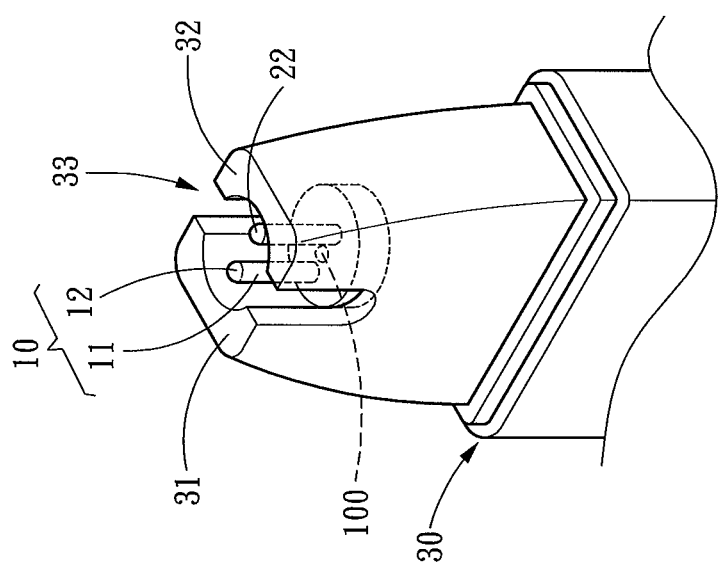
FIG. 3 is a partial schematic diagram of a housing according to an embodiment of the present invention.

FIG. 1 shows a schematic diagram of an appearance according to an embodiment of the present invention. FIG. 2 shows an exploded view according to an embodiment of the present invention. FIG. 3 shows a partial schematic diagram of a housing according to an embodiment of the present invention. Referring to FIGS. 1, 2 and 3, a detector for detecting sodium hypochlorite concentration according to an embodiment of the present invention includes a housing 30, a first electrode 10, and a second electrode 20. The first electrode 10 and the second electrode 20 are disposed opposite each other in the housing 30. The first electrode 10 includes a first detecting portion 11. The first detecting portion 11 exposes outside the housing 30 to extend outward, and includes a first semicircular end 12. The second electrode 20 includes a second detecting portion 21. The second detecting portion 21 exposes outside the housing 30 to extend outward, and includes a second semicircular end 22. In the embodiment, the first detection portion 11 and the second detecting portion 21 are arranged side by side and are spaced by a measurement distance.

The housing 30 includes a first outer wall 31, a second outer wall 32 and a measurement space 33. The first outer wall 31 is arranged at one side of the first detecting portion 11 away from the second detecting portion 21, and has a height greater than that of the first detecting portion 11. The second outer wall 32 is arranged at one side of the second detecting portion 21 away from the first detecting portion 11, and has a height greater than that of the second detecting portion 21. The measurement space 33 is formed between the first outer wall 31 and the second outer wall 32, and further separates the first detecting portion 11 from the second detecting portion 21 to form the measurement distance between the first detecting portion 11 and the second detecting portion 21.

Figure 4:
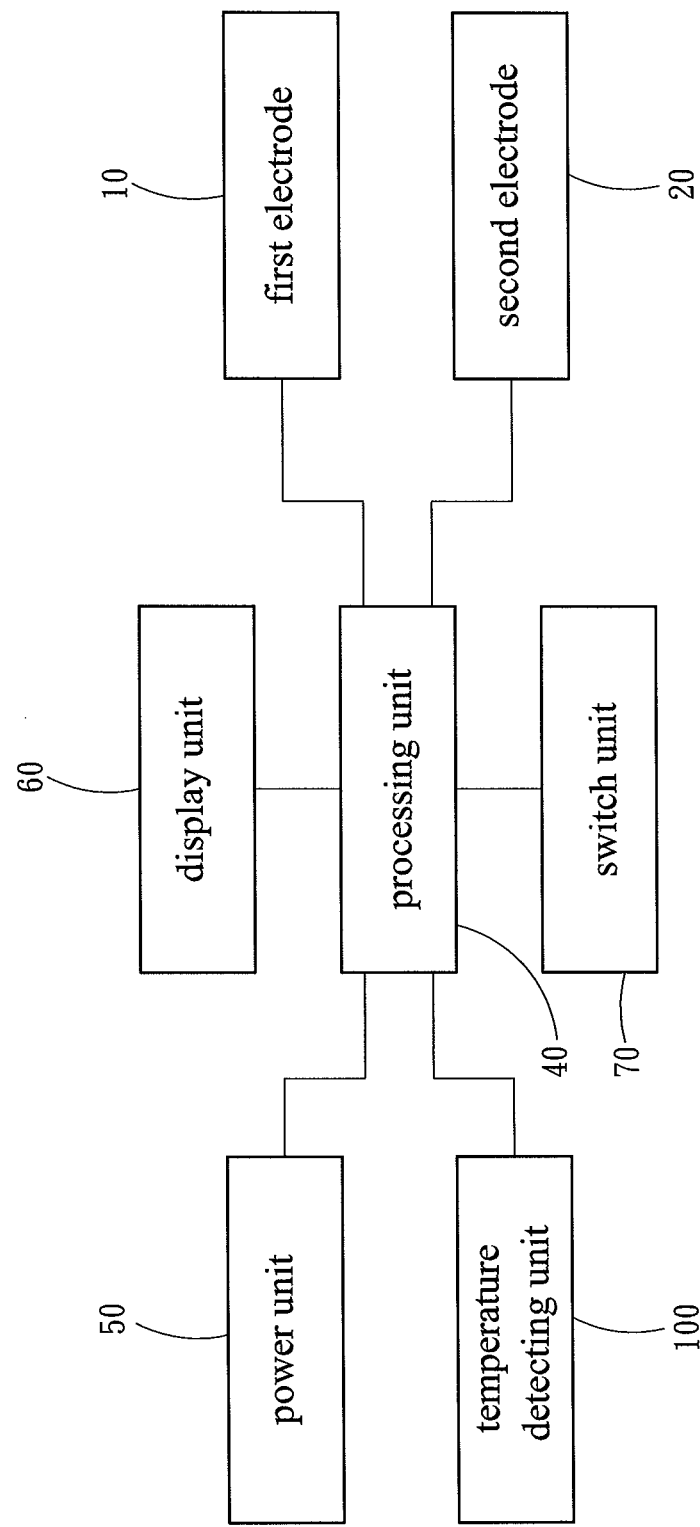
FIG. 4 is a schematic diagram of an electrical structure according to an embodiment of the present invention.

FIG. 4 shows a schematic diagram of an electrical structure according to an embodiment of the present invention. In one embodiment, the detector further includes a processing unit 40, a display unit 60, a power unit 50 and a switch unit 70. The processing unit 40, disposed in the housing 30, is electrically connected to the first electrode 10 and the second electrode 20. The display unit 60, disposed on the housing 30, is electrically connected to the processing unit 40, and is for displaying a current condition of the detector, e.g., the concentration calculated by the processing unit 40. The display unit 60 may be a liquid crystal display (LCD) screen. The power unit 50, exposing outside the housing 30, is electrically connected to the processing unit 40, and provides the processing unit 40 with an operating power. For example, the power unit 50 is a battery. The switch unit 70, mounted on the housing 30, is electrically connected to the processing unit 40, and is for activating the processing 40 for operations. For example, the switch unit 70 may be an activation button.

In the embodiment, the detector further includes a first cover 34 and a second cover 35. When the first electrode 10 and the second electrode 20 are not performing a measurement procedure, the first cover 34 may cover the first detecting portion 11 and the second detecting portion 21 that expose outside the housing 30 to connect to the housing 30, so as to prevent the first detecting portion 11 and the second detecting portion 21 from exposing to an exterior. The second cover 35 covers the power unit 50 exposing outside the housing 30 to connect with the housing 30. When the battery unit 50 is out power, the second cover 35 may be disengaged to replace the power unit 50. In one embodiment, for example, the first cover 34 and the second cover 35 are engaged with the housing 30 by a snapping fastening means.

FIG. 5 shows a schematic diagram of measuring concentration of a sodium hypochlorite solution according to an embodiment of the present invention. In the embodiment, a process for measuring the concentration of a sodium hypochlorite (NaOCl) solution 90 includes the following steps.

First of all, the switch unit 70 is activated to have the power unit 50 supply the operating power for operating the processing unit 40. The detector is placed in the sodium hypochlorite solution 90, allowing the first electrode 10 and the second electrode 20 to come into contact with the sodium hypochlorite solution 90. For example, the sodium hypochlorite solution 90 is allowed to enter the measurement space 33, such that the first detecting portion 11 and the second detecting portion 21 both come into contact with the sodium hypochlorite solution 90. As such, the measurement distance between the first detecting portion 11 and the second detecting portion 21 forms an electrical path 80.

Through measuring a plurality of ions in the sodium hypochlorite solution 90 transmitted in the electrical path 80, the processing unit 40 obtains a conductivity of the sodium hypochlorite solution 90. Please refer to the description below regarding the measurement of the conductivity. When dissolved in water, sodium hypochlorite is hydrolyzed into an alkyl solution (sodium hydroxide, NaOH) and a hypochlorous acid (HClO) to form the sodium hypochlorite solution 90. The ions of the sodium hypochlorite solution 90 include hydrogen ions ($H^+$), hydroxide ions ($OH^-$), sodium ions ($Na^+$) and hypochlorite ions ($ClO^-$). When sodium hypochlorite is dissolved in water, the reaction is represented by reaction formula (1) as:

$$NaOCl + H_2O \rightarrow NaOH + HClO \quad (1)$$

However, as the hypochlorous acid is a weak acid, the hypochlorous acid is partially separated into hydrogen ions and perchlorate ions ($OCl^-$) as represented by reaction formula (2):

$$HOCl \leftrightarrow H^+ + OCl^- \quad (2)$$

These ions are conductive substances called electrolyte. When electricity is conducted between the first electrode 10 and the second electrode 20, positive ions migrate to the cathode and negative ions migrate to the anode along the electrical path 80 to respectively generate an oxidation reduction reaction.

The overall conductive capability of the electrolyte is referred to the conductivity. The conductivity is represented by L, and is also a reciprocal of the resistance (R). That is:

$$L = 1/R \quad (3)$$

Like common solid conductors, electrolyte solutions also follow the Ohm's law, and thus equation (3) may be written as:

$$L = 1/r = 1/\rho \cdot A/\iota \quad (4)$$

In equation (4), $\rho$ is a resistance coefficient or specific resistivity of the solution, $\iota$ is a distance between the electrodes, A is a section area of the conducted solution, and the reciprocal of $\rho$ is referred to a conductivity coefficient, specific conductance or conductivity represented by $\kappa$; that is:

$$\kappa = 1/\rho \quad (5)$$

Therefore:

$$L = \kappa \cdot A/\iota \text{ (in a unit of } S \cdot m^{-1}) \quad (6)$$

The electrolyte concentration and the concentration of the sodium hypochlorite solution 90 are directly proportional, and both correspond to the specific conductivity. Further, the electrolyte concentration of the sodium hypochlorite solution 90 and the conductivity form a relationship of a non-linear function. Therefore, through experiments, the non-linear function can be defined. By numerical means, the processing unit 40 converts the conductivity to the solution concentration through the non-linear function, and displays a numerical value representing the concentration of the sodium hypochlorite solution 90 on the display unit 60.

Further, the conductivity of a liquid usually changes with a variation in temperature. Generally, based on a room temperature of 25° C. as a reference standard, the conductivity rises or drops by 2.1% for every 1° C. rise or drop in temperature. Hence, the detector may further include a temperature detecting unit 100, which is electrically connected to the processing unit 40. In the embodiment, for example, the temperature detecting unit 100 may be thermistor, and exposes in the measurement space 33 and is in contact with the sodium hypochlorite solution 90, so as to measure the temperature of the sodium hypochlorite solution 90. The processing unit 40 further performs automatic temperature compensation (ATC) procedure to calculate the correct concentration.

It should be noted that, with the first outer wall 31 and the second outer wall 32, a part of disturbances generated by the sodium hypochlorite solution 90 outside the measurement space 33 can be separated to prevent the value of the concentration from fluctuating drastically. The measurement space 33 further assists the sodium hypochlorite solution 90 to flow into the first outer wall 31 and the second outer wall 32 to come into contact with the first detecting portion 11 and the second detecting portion 21.

In conclusion, with the first electrode, the second electrode and the processing unit of the present invention, the ions in the sodium hypochlorite solution transmitted in the electrical path can be measured to obtain the conductivity and to further calculate the concentration of the sodium hypochlorite solution. Thus, compared to a conventional measurement apparatus adopting an optical detector, the detector of the present invention not only can be fabricated at low production costs, but also can instantly obtain the concentration through standalone measurement instead of having to be additionally connected to a computer. Further, with the first outer wall, the second outer wall and the measurement space of the present invention, the electrical path in the measurement space is measured, thereby preventing unnecessary disturbances outside the first outer wall and the second outer wall from affecting the measurement for the concentration.

What is claimed is:

1. A detector for detecting sodium hypochlorite concentration, comprising:
    a first electrode and a second electrode disposed opposite the first electrode, the first electrode and the second electrode being soaked in a sodium hypochlorite solution under detection, wherein an electrical path is formed among the first electrode, the sodium hypochlorite solution and the second electrode;
    a housing, accommodating the first electrode and the second electrode; the first electrode comprising a first detecting portion exposing outside the housing and extending outward from the housing, and the second electrode comprising a second detecting portion exposing outside the housing and extending outward from the housing; the housing comprising a first outer wall disposed at one side of the first detecting portion away from the second detecting portion, a second outer wall disposed at one side of the second detecting portion away from the first detecting portion, and a measurement space formed between the first outer wall and the second outer wall and separating the first detecting portion from the second detecting portion; the first outer wall being formed at a height greater than that of the first detecting portion, and the second outer wall being formed at a height greater than that of the second detecting portion; the electrical path being located in the measurement space; and a processing unit, electrically connected to the first electrode and the second electrode, configured to measure a plurality of ions in the sodium hypochlorite solution in the electrical path to obtain a conductivity of the sodium hypochlorite solution and to accordingly calculate the sodium hypochlorite concentration of the sodium hypochlorite solution.

2. The detector of claim 1, wherein the first detecting portion comprises a first semicircular end, and the second detecting portion comprises a second semicircular end.

3. The detector of claim 2 further comprising a first cover covering the first detecting portion and the second detecting portion and connecting to the housing.

4. The detector of claim 1, wherein the measurement space separates the first outer wall from the second outer wall.

5. The detector of claim 1 further comprising a power unit electrically connected to the processing unit to provide the processing unit with an operating power.

6. The detector of claim 5 further comprising a second cover covering the power unit which exposes outside the housing, wherein the second cover is connecting to the housing.

7. The detector of claim 1 further comprising a display unit electrically connected to the processing unit for displaying the detected concentration.

8. The detector of claim 7, wherein the display unit is disposed on the housing.

9. The detector of claim 1 further comprising a switch unit electrically connected to the processing unit for activating the processing unit.

10. The detector of claim 1 further comprising a temperature detecting unit electrically connected to the processing unit for detecting a temperature of the sodium hypochlorite solution.

* * * * *